(12) United States Patent
Adachi et al.

(10) Patent No.: US 6,674,528 B2
(45) Date of Patent: Jan. 6, 2004

(54) METHOD AND APPARATUS FOR MEASURING SUSPENDED PARTICULATE MATTER

(75) Inventors: Motoaki Adachi, Ibaraki (JP); Kikuo Okuyama, Higashihiroshima (JP); Shinichiro Totoki, Kyoto (JP); Michio Higuchi, Kyoto (JP); Haruo Shimaoka, Nara (JP); Akihiro Fukai, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/196,629

(22) Filed: Jul. 16, 2002

(65) Prior Publication Data

US 2003/0016356 A1 Jan. 23, 2003

(30) Foreign Application Priority Data

Jul. 17, 2001 (JP) .......................................... 2001-216198

(51) Int. Cl.$^7$ .......................... G01D 15/02; G01D 21/00
(52) U.S. Cl. ...................................... 356/336; 356/338
(58) Field of Search ................................ 356/335–338, 356/340, 342, 343; 250/574, 573, 222.2

(56) References Cited

U.S. PATENT DOCUMENTS

| | | | | |
|---|---|---|---|---|
| 3,520,172 A | | 7/1970 | Liu et al. | |
| 3,740,553 A | * | 6/1973 | Whetten | ............. 250/292 |
| 4,917,494 A | * | 4/1990 | Poole et al. | ............. 356/335 |
| 5,471,299 A | * | 11/1995 | Kaye et al. | ............. 356/336 |
| 5,561,520 A | * | 10/1996 | Williams | ............. 356/335 |
| 5,855,652 A | | 1/1999 | Talley | |
| 6,211,956 B1 | * | 4/2001 | Nicoli | ............. 356/337 |
| 6,400,453 B1 | * | 6/2002 | Hansen | ............. 356/237.1 |
| 6,417,920 B1 | * | 7/2002 | Shimaoka | ............. 356/336 |
| 6,469,786 B2 | * | 10/2002 | Shimaoka | ............. 356/336 |
| 6,473,178 B2 | * | 10/2002 | Shimaoka | ............. 356/336 |

OTHER PUBLICATIONS

Patent Abstracts of Japan, Publication No.: 11183356, Publication Date: Sep. 7, 1999, Laser Diffraction and Scattering Type Particle Size Distribution Measuring Device.
Patent Abstracts of Japan, Publication No.: 2001033375, Publication Date: Sep. 2, 2001, Laser Diffraction/Scattering Type Grain Size Distribution–Measuring Device.
Patent Abstracts of Japan, Publication No.: 2002116134, Publication Date: Apr. 19, 2002, Measuring Apparatus for Suspended Particulate Matter.

* cited by examiner

Primary Examiner—Michael P. Stafira
(74) Attorney, Agent, or Firm—Rankin, Hill, Porter & Clark LLP

(57) ABSTRACT

Suspended particulate matter in the atmospheric air is sucked into a container by a pump. The suspended particulate matter in the atmospheric air in the container is electrically charged so as to electrically collect it. The collected suspended particulate matter is irradiated with laser beams under the condition that the collected suspended particulate matter is dispersed at an appropriate concentration. A spatial intensity distribution of diffracted and scattered light obtained by irradiating laser beams to the suspended particulate matter is measured. A particle size distribution of the suspended particulate matter P is found from the result of measurement.

7 Claims, 2 Drawing Sheets

METHOD AND APPARATUS FOR MEASURING SUSPENDED PARTICULATE MATTER

BACKGROUND OF THE INVENTION

1. Field of the Invention

The present invention relates to a method and an apparatus for measuring a particle size distribution of suspended particulate matter existing in the atmospheric air. More particularly, the present invention relates to a method and an apparatus for measuring suspended particulate matter capable of measuring a particle size distribution of the suspended particulate matter in a wide range of particle size at high resolution.

2. Description of the Related Art

Suspended dust in the atmospheric air, the particle size of which is not more than 10 μm, is referred to as suspended particulate matter (SPM). Although this suspended particulate matter contains scattered mud, most of the suspended particulate matter is black smoke, which has been exhausted from Diesel engine cars, unburnt fuel and sulfur compounds. In the Kanto District, about 35% of the suspended particulate matter is exhausted from Diesel engine cars. It is said that the suspended particulate matter is harmful to human's health. Especially, particulate matter, which is contained in exhaust gas exhausted from Diesel engine cars, is referred to as DEP (Diesel Exhaust Particles). Particulate matter of small particle size, the size of which is not more than 2.5 μm, is referred to as fine particulate matter (PM 2.5), which has been actively investigated in Europe and America. It is said that most of this PM 2.5 is exhausted from Diesel engine cars.

As an apparatus for measuring a particle size distribution of the above suspended particulate matter (SPM) or fine particulate matter (PM 2.5) in the atmospheric air, a measuring apparatus based on the cascade impacter system has been conventionally put into practical use. In this measuring apparatus based on the cascade impacter system, fluid including particulates is made to collide with a collecting plate so as to suddenly change a direction of the current of fluid, so that the particulates can be separated from the fluid. In this measuring apparatus, impacters, the particle sizes at the collecting efficiency of 50% of which are different each other, are connected with each other in series so that they can be formed into a multiple stage. Then, the particle size at the collecting efficiency of 50% of each stage is used as a representative particle size, and a particle size distribution in the fluid is found from the result of measurement of collection of particulates having the representative particle size at each stage.

In this connection, in the measuring apparatus according to the cascade impacter system used for the measurement of SPM and PM 2.5, the following problems may be encountered. An upper limit of measuring the particle size is set at about 10 μm in the principle, and further resolution of the particle size is determined by the number of the collecting plates. Therefore, it is impossible to measure a particle size distribution at high resolution.

SUMMARY OF THE INVENTION

It is an object of the present invention to provide a method and an apparatus for measuring suspended particulate matter capable of measuring a distribution of particle size of suspended particulate matter (SPM) and fine particulate matter (PM 2.5) in the atmospheric air in a wide range of particle size including the particle size not less than 10 μm at high resolution.

In order to accomplish the above object, the present invention provides a method for measuring suspended particulate matter in the atmospheric air, the method comprising: sucking suspended particulate matter in the atmospheric air into a container; electrically charging the suspended particulate matter in the atmospheric air in the container; electrically collecting the charged suspended particulate matter; irradiating the collected suspended particulate matter with laser beams under the condition that the collected suspended particulate matter is dispersed; measuring a spatial intensity distribution of diffracted and scattered light obtained by irradiating the suspended particulate matter with laser beams; and calculating a particle size distribution of the suspended particulate matter from the result of the measurement.

The method for measuring suspended particulate matter in the atmospheric air according to the present invention, preferably, further comprises: dispersing the collected suspended particulate matter in medium fluid, wherein the suspended particulate matter dispersed in the medium fluid is irradiated with the laser beams.

Alternatively, the method for measuring suspended particulate matter in the atmospheric air according to the present invention, preferably, further comprises: causing the suspended particulate matter to adhere onto a surface of a transparent plate in the container, wherein the transparent plate, onto which the suspended particulate matter adheres, is irradiated with laser beams. Any of the above methods can be adopted.

In order to accomplish the above object, the present invention also provides an apparatus for measuring suspended particulate matter in the atmospheric air, the comprising: a container; a pump for sucking the atmospheric air into the container; a discharging electrode, which is arranged in the container, for electrically charging the suspended particulate matter in the container by generating single-pole ions; a dust collecting electrode, which has an electric potential difference with respect to the discharging electrode, for collecting the suspended particulate matter, which has been electrically charged in the container by the discharging electrode; a dispersing mechanism for dispersing the suspended particulate matter collected by the dust collecting electrode; an irradiating optical system for irradiating the dispersed suspended particulate matter with laser beams; a measuring optical system for measuring a spatial intensity distribution of light which has been diffracted and scattered by the suspended particulate matter when the suspended particulate matter is irradiated with laser beams; and a calculation section for calculating a particle size distribution of the collected suspended particulate matter from the result of measurement.

According to the apparatus for measuring suspended particulate matter according to the present invention, it is preferable that the dispersing mechanism has a dispersing tank including medium fluid accommodated therein. Alternatively, it is also preferable that the dispersing mechanism has a transparent plate, onto a surface of which the suspended particulate matter adheres.

The pump, preferably, includes a pneumatic machine capable of sucking and feeding atmospheric air forcibly. Specifically, the pump includes a compressor or blower.

As medium solution in which the collected suspended particulate matter is dispersed, it is possible to use clean water such as distilled water, organic solvent or organic solvent to which a dispersing agent such as a surface active agent is added.

According to the present invention, the measurement of a particle size distribution based on the method of laser beam diffraction and scattering, which is capable of measuring the particle size distribution at high resolution in a wide particle size range, is applied to the measurement of a particle size distribution of suspended particulate matter in the atmospheric air. Further, in order to obtain a sufficiently high intensity of diffracted and scattered light in the irradiation of laser beams, suspended particulate matter in the atmospheric air is not directly irradiated with laser beams but suspended particulate matter is irradiated with laser beams under the condition that the suspended particulate matter is effectively collected and diffused at a sufficiently high concentration so as to accomplish the object of the present invention.

In the case of a particle size analyzer based on the laser diffraction method, in general, a spatial intensity distribution of diffracted and scattered light obtained by the irradiation of laser beams to a group of particulates in a scattered condition is measured. By utilizing that the light intensity distribution agrees with Mie's Scattering Theory or Fraunhofer's Diffraction Theory, a particle size distribution of the group of particulates to be measured is found by the calculation based on Mie's Scattering Theory or Fraunhofer's Diffraction Theory according to the result of the measurement of the spatial intensity distribution of diffracted and scattered light. According to, this particle size analyzer based on the laser diffraction method, when the concentration of the group of particulates to be measured in the medium, in which the group of particulates to be measured is scattered, is kept in an appropriate range, it possible to find a particle size distribution at high resolution in a wide particle size range.

However, in the case of suspended particulate matter in the atmospheric air, even when diffracted and scattered light is measured by directly irradiating laser beams to the suspended particulate matter in the atmospheric air, it is impossible to obtain a sufficiently high intensity of diffracted and scattered light for finding the particle size distribution of the suspended particulate matter because the concentration of suspended particulate matter in the atmospheric air is too low.

Therefore, according to the present invention, the spatial intensity distribution of diffracted and scattered light obtained by the irradiation of laser beams to suspended particulate matter is measured as follows. The atmospheric air is sucked into a container, and suspended particulate matter contained in the atmospheric air in the container is electrically collected. That is, the discharging electrode generates single-pole ions, and suspended particulate matter is electrically charged by the single-pole ions generated from the discharging electrode. Then, a dust collecting electrode, to which a predetermined electric potential difference with respect to the discharging electrode is given, is arranged, and the electrically charged suspended particulate matter is collected by the dust collecting electrode. The thus collected suspended particulate matter is dispersed into a concentration range appropriate for the particle size distribution analysis based on the laser diffraction method. The thus dispersed suspended particulate matter is irradiated with laser beams, and the spatial intensity distribution of diffracted and scattered light is measured. Due to the foregoing, it is possible to find a particle size distribution of suspended particulate matter at high resolution in a wide particle size range which is identical with that of the common particle size analysis based on the laser diffraction method. That is, it is possible to find a particle size distribution of suspended particulate matter at high resolution in a wide particle size range from sub-micron to 10 $\mu$m or greater.

Preferably, the collected suspended particulate matter is dispersed in medium fluid and the suspended particulate matter is irradiated with laser beams in a dispersed state so as to measure diffracted and scattered light. Alternatively, the suspended particulate matter is being collected, while adhering onto a surface of a transparent plate so that the suspended particulate matter is dispersed. Then, the suspended particulate matter is irradiated with laser beams in a dispersed state so as to measure diffracted and scattered light. By any of these methods, diffracted and scattered light, which has been diffracted and scattered by the collected suspended particulate matter, can be measured with high accuracy.

According to the present invention, since the atmospheric air is sucked into a container by a pump and suspended particulate matter contained in the atmospheric air is electrically charged and collected, a volume of atmospheric air fed into the container can be easily grasped by the flow rate and the drive time of the pump, and further almost all suspended particulate matter in the atmospheric air fed into the container can be collected. Accordingly, a quantity of suspended particulate matter existing in a constant volume of atmospheric air for every particle size can be simply found.

DETAILED DESCRIPTION OF THE INVENTION

Figure 1:
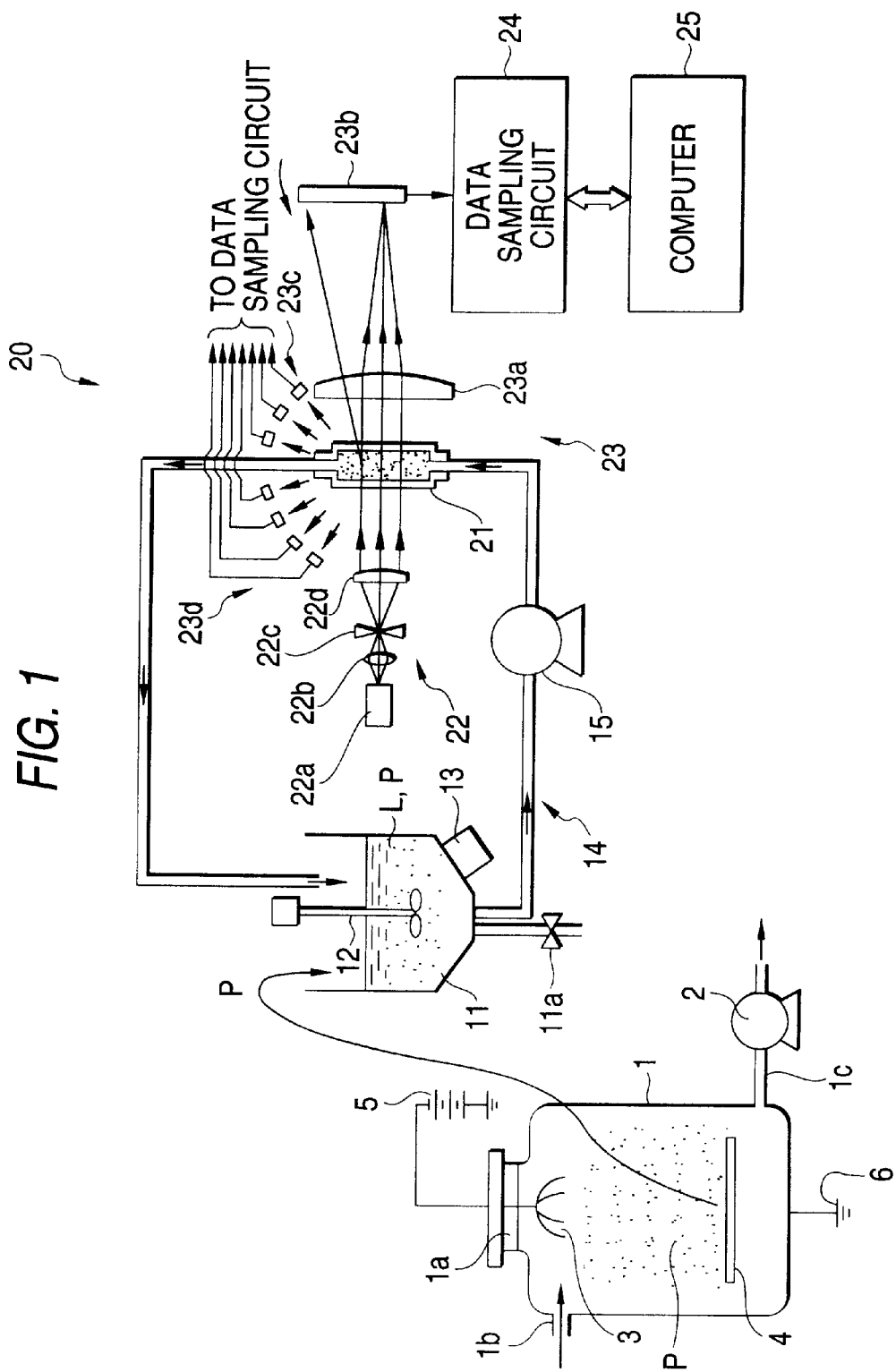
FIG. 1 is an arrangement view of a suspended particulate matter measuring apparatus according to an embodiment of the present invention.

Referring to the drawings, an embodiment of the present invention will be explained below.

FIG. 1 is an arrangement view of a suspended particulate matter measuring apparatus according to an embodiment of the present invention. A schematic drawing showing an optical constitution and piping constitution and a block diagram showing an electrical constitution are jointly shown in FIG. 1.

The suspended particulate matter measuring apparatus comprises a collecting container 1, a pump 2, a discharging electrode 3, a dust collecting electrode 4, a high voltage power source 5, a grounding potential 6, a dispersing tank 11, a circulating pipe 14, a circulating pump 15, and a particle size analyzer 20. The collecting container 1 has a cover 1a capable of being freely opened and closed, an inlet 1b of the atmospheric air and a communicating port 1c to a suction port of the pump (compressor for collecting particulates) 2. Under the condition that the cover 1a is closed, the atmospheric air is sucked into the collecting container 1 via the inlet 1b when the pump 2 is driven. In this collecting container 1, there are provided the discharging electrode 3 in the upper portion and the dust collecting electrode 4, which is opposed to the discharging electrode 3, in the lower portion. The discharging electrode 3 is impressed with a high voltage by the high voltage power source 5. Due to the foregoing, the air in the neighborhood of the discharging electrode 3 is ionized, and single-pole ions are generated.

On the other hand, in this example, the dust collecting electrode 4 is connected with the grounding potential 6. By the difference of potential between the dust collecting electrode 4 and the discharging electrode 3, single-pole ions are moved to the dust collecting electrode 4. In this process, the single-pole ions come into contact with suspended particulate matter P contained in the atmospheric air in the dust collecting container 1, and suspended particulate matter P is electrically charged. The thus electrically charged suspended particulate matter P is moved to the dust collecting electrode 4 by the potential difference between the discharging electrode 3 and the dust collecting electrode 4. Therefore, the electrically charged suspended particulate matter P is collected onto the dust collecting electrode 4.

Figure 2:
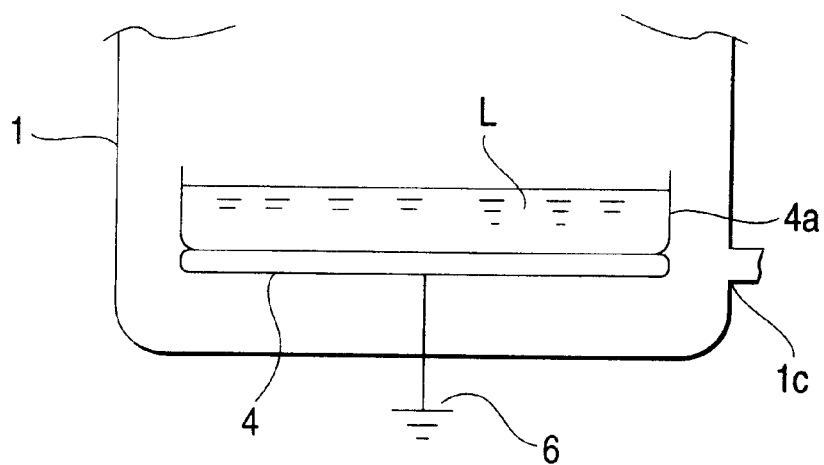
FIG. 2 is an arrangement view showing a primary portion of a suspended particulate matter measuring apparatus according to another embodiment of the present invention.

The suspended particulate matter P, which has been collected onto the dust collecting electrode 4, is dispersed in the dispersing tank 11. In the dispersing tank 11, for example, distilled water or organic solvent or medium fluid L, to which a dispersing agent such as a surface active agent is added, is accommodated. This suspended particulate matter P is dispersed in the dispersing tank 11 in such a manner that the cover 1a is detached from the collecting container 1 and the dust collecting electrode 4 is manually taken outside from the collecting container 1, and then the dust collecting electrode 4 is dipped in medium liquid L in the dispersing tank 11, so that suspended particulate matter P attached to the dust collecting electrode 4 is transferred into medium liquid L. Alternatively, as shown in the arrangement view showing a primary portion of the apparatus in FIG. 2, a Petri-dish-shaped member 4a made of conductive material is mounted on a surface of the dust collecting electrode 4, and the same medium liquid L as the medium liquid L in the dispersing tank 11 is accommodated in the Petri-dish-shaped member 4a. Suspended particulate matter P can be collected by medium liquid L accommodated in the Petri-dish-shaped member 4a. Medium liquid L in the Petri-dish-shaped member 4a containing suspended particulate matter P is introduced into the dispersing tank 11 by a pump not shown. Alternatively, medium liquid L in the Petri-dish-shaped member 4a containing suspended particulate matter P is manually transferred into the dispersing tank 11.

The dispersing tank 11 has an agitator 12 and an ultrasonic oscillator 13. A bottom portion of the dispersing tank 11 is communicated with one end portion of the circulating pipe 14. The circulating pipe 14 is communicated with an entrance of a flow cell 21 of a particle size analyzer based on the laser diffraction method 20. Further, the circulating pipe 14 of the exit of this flow cell 21 is open to an upper portion of the dispersing tank 11. The dispersing tank 11 also has a drainage valve 11a for draining the content of the tank at the bottom portion thereof.

After suspended particulate matter P has been transferred into medium liquid L accommodated in the dispersing tank 11, the agitator 12 and ultrasonic oscillator 13 are driven. Due to the foregoing, suspended, particulate matter P can be uniformly dispersed in medium liquid L, and bubbles can be removed from medium liquid L.

When the circulating pump 15 is driven, medium liquid L and suspended particulate matter P dispersing in medium liquid L are made to flow into the flow cell 21 via the circulating pipe 14 and returned into the dispersing tank 11.

The particle size analyzer based on the laser diffraction method 20 includes the flow cell 21 described before, an irradiating optical system 22, a measuring optical system 23, a data sampling circuit 24 and a computer 25. The irradiating optical system 22 irradiates laser beams to the flow cell 21. The measuring optical system 23 measures a spatial intensity distribution of diffracted and scattered light of laser beams sent from the irradiating optical system 22. The data sampling circuit 24 conducts data sampling on an output of the measuring optical system 23. The computer 25 calculates a particle size distribution of a group of particulates contained in medium liquid L by using the spatial intensity distribution data of diffracted and scattered light which have been sampled by the data sampling circuit 24.

The irradiating optical system 22 includes a laser beam source 22a, a condenser lens 22b, a spatial filter 22c, and a collimate lens 22d. By this irradiating optical system 22, laser beams outputted from the laser beam source 22a are formed into a parallel light flux and irradiated to the flow cell 21. Laser beams irradiated to the flow cell 21 are diffracted and scattered by suspended particulate matter P in medium liquid L flowing in the flow cell 21. The spatial intensity distribution of this diffracted and scattered light is measured by the measurement optical system 23.

The measuring optical system 23 includes a condenser lens 23a, a ring detector 23b, a group of front wide angle scattered light sensors 23c, and a group of side/rear scattered light sensors 23d. The condenser lens 23a and the ring detector 23b are arranged on the optical axis of the irradiating optical system 22 being opposed to the flow cell 21. The group of front wide angle scattered light sensors 23c are arranged outside the optical axis of the irradiating optical system 22, and arranged on the front of the flow cell 21 (on the ring detector 23b side). The group of side/rear scattered light sensors 23d are arranged on the side and at the rear of the flow cell 21 (on the irradiating optical system 22 side). The ring detector 23b is a light sensor array in which light sensors having a light receiving face, the shape of which is ring-shaped or ½-ring-shaped or ¼-ring-shaped, the radiuses of curvature of which are different from each other, are concentrically arranged. The ring detector 23b is capable of detecting an intensity distribution of diffracted and scattered light in a predetermined front angle condensed by the condenser lens 23a. Accordingly, by this measuring optical system 23 composed of the group of sensors, it is possible to measure a spatial intensity distribution of diffracted and scattered light, which is diffracted and scattered by suspended particulate matter P dispersed in medium liquid L in the flow cell 21, in a wide range from a front minute angle to the rear.

A light intensity detecting signal for each diffraction and scattering angle, which is detected by the measuring optical system 23, is amplified and digitized by the data sampling circuit 24 having an amplifier and A-D converter and taken into the computer 25 as spatial intensity distribution data of diffracted and scattered light.

In the computer 25, by using this spatial intensity distribution of diffracted and scattered light, a particle size distribution of suspended particulate matter, which causes diffraction and scattering of laser beams, is calculated by the method of calculation according to Mie's Scattering Theory and Fraunhofer's Diffraction Theory which is well known in the particle size analysis based on the laser diffraction method.

In the above constitution, a total volume of atmospheric air fed into the collecting container 1 can be grasped from the flow rate per unit time and the drive time of the pump. By appropriately setting the total volume of atmospheric air fed into the collecting container 1, when suspended particulate matter P collected by the dust collecting electrode 4 is dispersed in medium liquid L accommodated in the dispersing tank 11, the concentration of suspended particulate matter P in medium liquid 1 can be made to be value at which a spatial intensity distribution of diffracted and scattered light can be sufficiently measured by the measuring optical system 22.

According to the measurement of the particle size distribution conducted by this particle size analyzer based on the laser diffraction method 20, it is possible to measure a particle size distribution at high resolution in a wide particle size range from sub-micron to 10 $\mu$m or greater.

When the following motions are repeated at regular intervals, it becomes possible to continuously monitor circumstances of suspended particulate matter in the atmospheric air. A predetermined volume of atmospheric air is sucked into the collecting container 1; suspended particulate matter P is collected onto the dust collecting electrode 4; the thus collected suspended particulate matter P is dispersed into medium liquid L accommodated in the dispersing tank 11; suspended particulate matter P is irradiated with laser beams; a spatial intensity distribution of diffracted and scattered light is measured so as to find a particle size distribution; the drainage valve 11a is opened so as to drain liquid inside the dispersing tank 11; new clean medium fluid L is poured into the dispersing tank 11; suspended particulate matter, which has been newly collected in the collecting container 1, is dispersed in this medium liquid L; and a measuring motion to measure a spatial intensity distribution of diffracted and scattered light is successively started.

When a total volume of atmospheric air to be fed into the dust collecting container 1 is made constant at each measuring motion, an absolute intensity of diffracted and scattered light obtained in the measurement of each time is correlated with the concentration of suspended particulate matter P in the atmospheric air. Therefore, from a change in the absolute intensity of diffracted and scattered light, it possible to monitor a change in the concentration of suspended particulate matter P in the atmospheric air with time.

When calibration is conducted with reference particles, the number contained in unit volume of medium liquid L of which has already been known, it is possible to calculate a relation of the particle size distribution of suspended particulate matter P contained in the atmospheric air of unit volume and the number of the particles of each particle size, from the total volume of atmospheric air required for collecting suspended particulate matter dispersed in medium liquid L and from the absolute intensity of diffracted and scattered light obtained at that time.

In the above embodiment, the particle size distribution of suspended particulate matter P is found from the spatial intensity distribution of diffracted and scattered light obtained when suspended particulate matter P collected onto the dust collecting electrode 4 in the collecting container 1 is dispersed in medium liquid L in the dispersing tank 11 and irradiated with laser beams. However, the present invention is not limited to the above wet type measurement of measuring a particle size distribution by the diffraction and scattering of laser beams but the present invention can be applied to a dry type measurement of measuring a particle size distribution by the diffraction and scattering of laser beams in which medium liquid is not used.

Figure 3:
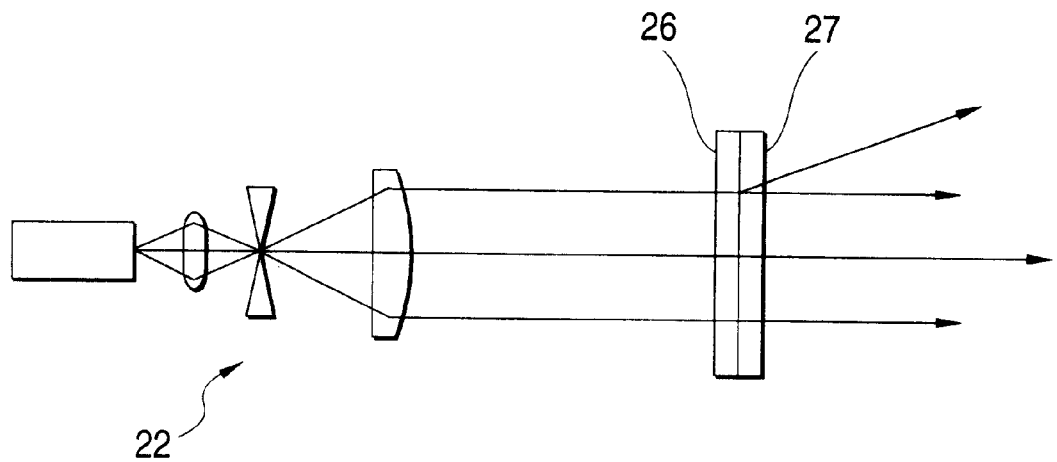
FIG. 3 is an arrangement view showing a primary portion of a suspended particulate matter measuring apparatus according to still another embodiment of the present invention.

In the case of adopting the dry type measurement method, the following method is preferably adopted. A transparent plate is used, and suspended particulate matter P is dispersed when it is collected onto a surface of the transparent plate, and suspended particulate matter P, which is dispersed on the transparent plate, is irradiated with laser beams. That is, the transparent plate is arranged on, the dust collecting electrode 4 in the collecting container 1, and suspended particulate matter P in the atmospheric air, which has been fed into the collecting container 1 and electrically charged, is collected onto the transparent plate. FIG. 3 shows a primary constitution of the particle size analyzer based on the laser diffraction method used for the dry measurement. As shown in FIG. 3, instead of the flow cell 21 shown in the apparatus constitution of FIG. 1, the transparent plate 26, to which suspended particulate matter P collected in the collecting container 1 adheres, is arranged on the optical path of the irradiating optical system 22 and irradiated with laser beams. At this time, in order to prevent suspended particulate matter P from dropping from the surface of the transparent plate 26, one more transparent plate 27 may be used if necessary as shown in FIG. 3 so that the suspended particulate matter P can be interposed between the two transparent plates 26 and 27.

Even in the case of the above dry measurement method, as long as the concentration (quantity of particulates existing per unit area) of suspended particulate matter P on the transparent plate 26 is an appropriate value, in the same manner as that of the aforementioned wet type measurement method, it is possible to accurately measure a spatial intensity distribution of laser beams diffracted and scattered by suspended particulate matter P. Therefore, the same effect as that of the embodiment described before can be provided.

As described above, according to the present invention, the atmospheric air is sucked into the collecting container by a pump, and suspended particulate matter contained in the atmospheric air is electrically charged by the discharging electrode arranged in the collecting container so that the suspended particulate matter is collected by the dust collecting electrode. The thus collected suspended particulate matter is dispersed in medium fluid at an appropriate concentration or alternatively the thus collected suspended particulate matter is made to adhere onto a surface of the transparent plate and dispersed. Then, the dispersed suspended particulate matter is irradiated with laser beams and a spatial intensity distribution of light diffracted and scattered by the suspended particulate matter is measured. By the result of the measurement, a particle size distribution of the suspended particulate matter is found according to the principle of the laser diffraction method. Accordingly, compared with the particle size distribution measurement method conducted by the conventional cascade type impacter, the method of the present invention is advantageous in that the resolution of the particle size can be greatly enhanced and further the particle size distribution in the particle size range not less than 10 $\mu$m can be measured.

What is claimed is:

1. A method for measuring suspended particulate matter in the atmospheric air, the method comprising:
   sucking suspended particulate matter in the atmospheric air into a container;
   electrically charging the suspended particulate matter in the atmospheric air in the container;
   electrically collecting the charged suspended particulate matter;
   irradiating the collected suspended particulate matter with laser beams under the condition that the collected suspended particulate matter is dispersed;

measuring a spatial intensity distribution of diffracted and scattered light obtained by irradiating the suspended particulate matter with laser beams; and calculating a particle size distribution of the suspended particulate matter from the result of the measurement.

2. The method for measuring suspended particulate matter in the atmospheric air according to claim 1, further comprising:

dispersing the collected suspended particulate matter in medium fluid, wherein the suspended particulate matter dispersed in the medium fluid is irradiated with the laser beams.

3. The method for measuring suspended particulate matter in the atmospheric air according to claim 1, further comprising:

causing the suspended particulate matter to adhere onto a surface of a transparent plate in the container, wherein the transparent plate, onto which the suspended particulate matter adheres, is irradiated with laser beams.

4. An apparatus for measuring suspended particulate matter in the atmospheric air, the comprising:

a container;

a pump for sucking the atmospheric air into the container;

a discharging electrode, which is arranged in the container, for electrically charging the suspended particulate matter in the container by generating single-pole ions;

a dust collecting electrode, which has an electric potential difference with respect to the discharging electrode, for collecting the suspended particulate matter, which has been electrically charged in the container by the discharging electrode;

a dispersing mechanism for dispersing the suspended particulate matter collected by the dust collecting electrode;

an irradiating optical system for irradiating the dispersed suspended particulate matter with laser beams;

a measuring optical system for measuring a spatial intensity distribution of light which has been diffracted and scattered by the suspended particulate matter when the suspended particulate matter is irradiated with laser beams; and a calculation section for calculating a particle size distribution of the collected suspended particulate matter from the result of measurement.

5. The apparatus for measuring suspended particulate matter in the atmospheric air according to claim 4, wherein the dispersing mechanism has a dispersing tank including medium fluid accommodated therein.

6. The apparatus for measuring suspended particulate matter in the atmospheric air according to claim 4, wherein the dispersing mechanism has a transparent plate, onto a surface of which the suspended particulate matter adheres.

7. The apparatus for measuring suspended particulate matter in the atmospheric air according to claim 5, wherein the dispersing tank is disposed on the dust collecting electrode.

* * * * *